United States Patent [19]
Cartwright et al.

[11] 4,401,460
[45] Aug. 30, 1983

[54] HERBICIDAL PHENOXYPYRIDINES

[75] Inventors: David Cartwright, Woodley; David Collins, Crowthorne, both of England

[73] Assignee: Imperial Chemical Industries PLC, London, England

[21] Appl. No.: 295,301

[22] Filed: Aug. 24, 1981

Related U.S. Application Data

[62] Division of Ser. No. 156,075, Jun. 2, 1980, Pat. No. 4,308,053.

[30] Foreign Application Priority Data

Jun. 20, 1979 [GB] United Kingdom ................ 7921505

[51] Int. Cl.$^3$ .................... C07D 213/64; A01N 43/40
[52] U.S. Cl. ....................................... 71/94; 546/291; 546/300; 546/302
[58] Field of Search ............................ 546/291; 71/94

[56] References Cited

U.S. PATENT DOCUMENTS

| 4,083,714 | 4/1978 | Takahashi et al. | 71/94 |
| 4,133,675 | 1/1979 | Schurter et al. | 71/94 |
| 4,246,419 | 1/1981 | Cartwright et al. | 546/291 |
| 4,253,866 | 3/1981 | Schurter et al. | 71/94 |
| 4,308,053 | 12/1981 | Cartwright | 71/94 |

FOREIGN PATENT DOCUMENTS

| 176 | 1/1979 | European Pat. Off. | 71/94 |
| 1473 | 4/1979 | European Pat. Off. | 71/94 |
| 3416 | 8/1979 | European Pat. Off. | 71/118 |
| 5709 | 12/1979 | European Pat. Off. | 71/124 |
| 2258382 | 8/1975 | France | 546/300 |
| 2025945 | 1/1980 | United Kingdom | 546/293 |

Primary Examiner—Alan L. Rotman
Attorney, Agent, or Firm—Cushman, Darby & Cushman

[57] ABSTRACT

This invention relates to phenoxypyridine derivatives useful as herbicides, and to herbicidal compositions and processes utilizing them.

6 Claims, No Drawings

HERBICIDAL PHENOXYPYRIDINES

This application is a division of application Ser. No. 156,075, filed June 2, 1980, now U.S. Pat. No. 4,308,053.

DETAILED DISCLOSURE

According to the present invention, there are provided phenoxypyridines of the formula (I):

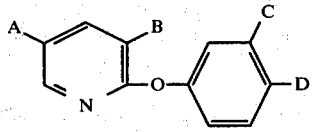
(I)

wherein each of A and B is a hydrogen atom, a fluorine, chlorine, bromine or iodine atom, or a difluoromethyl, chlorodifluoromethyl or trifluoromethyl group, provided that at least one of A and B is a halomethyl group; C is (a) a COZ group wherein Z is OH; OM wherein M is a cation; $OR^3$ wherein $R^3$ is a $C_1$–$C_{12}$ alkyl radical optionally substituted by hydroxy or $C_1$–$C_{12}$ alkoxy; or a group $NR^4R^5$ wherein $R^4$ is hydrogen, $C_1$–$C_{12}$ alkyl, or $C_3$–$C_{12}$ alkenyl, and $R^5$ is as defined as for $R^4$ but may also be alkylcarbonyl of 2 to 6 carbon atoms or alkanesulphonyl of 1 to 6 carbon atoms; (b) a fluorine, chlorine, bromine, or iodine atom; or (c) an $-OR^1$, $-SR^1$ or $-NR^1R^2$ group wherein $R^1$ is an alkenyl group of 3 to 12 carbon atoms, an alkyl group of 1 to 12 carbon atoms, or an alkyl group of 1 to 12 carbon atoms substituted by one or more of the following: phenyl; $-COZ$ as defined above; $C_1$–$C_{12}$ alkoxy; $C_1$–$C_{12}$ alkylthio; or mono- or di- $C_1$–$C_{12}$ alkylamino and $R^2$ is hydrogen; $C_3$–$C_{12}$ alkenyl; $C_1$–$C_{12}$ alkyl or $C_2$–$C_6$ alkylcarbonyl; and D is hydrogen, fluorine, chlorine, bromine, iodine, nitro, or cyano, provided that when A is $CF_3$, B is chlorine, and D is halogen, nitro, or cyano, C is not (a) a $C_1$–$C_4$ alkoxy group, a $-COOR^7$ group wherein $R^7$ is hydrogen, a cation, or a $C_1$–$C_4$ alkyl group; or (b) an

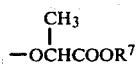

group wherein $R^7$ is hydrogen, a cation, or a $C_1$–$C_4$ alkyl group.

The cation M may be for example an alkali metal, an alkaline earth metal, an ammonium ion, or a substituted ammonium ion.

A sub-group of compounds according to the invention includes those compounds in which A is a trifluoromethyl group, B is hydrogen or chlorine, and C is an

group or a $-CONHSO_2CH_3$ group.

Particular examples of compounds according to the invention are listed in Table I below.

TABLE I

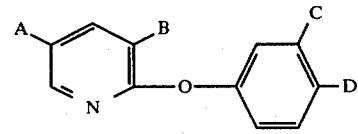

| Compound No. | A | B | C | D | Melting Point °C. |
|---|---|---|---|---|---|
| 1 | $CF_3$ | H | $CH_3$<br>$\mid$<br>$-OCHCO_2C_2H_5$ | H | Oil |
| 2 | $ClCF_2$ | H | $CH_3$<br>$\mid$<br>$-OCHCO_2C_2H_5$ | H | Oil |
| 3 | $CF_3$ | Cl | $CONHSO_2CH_3$ | $NO_2$ | 175–176 |
| 4 | $CF_3$ | H | $CONHSO_2CH_3$ | H | 174 |
| 5 | $CF_3$ | H | $CO_2H$ | $NO_2$ | 154 |
| 6 | $CF_3$ | H | $CONHSO_2CH_3$ | $NO_2$ | 155 |
| 7 | $CF_3$ | Cl | $CO_2H$ | H | 158 |
| 8 | $CF_3$ | Cl | $CONHSO_2CH_3$ | H | 174 |
| 9 | $CF_3$ | Cl | $CH_3$<br>$\mid$<br>$-OCHCONHSO_2CH_3$ | $NO_2$ | 144–145 |
| 10 | $CF_3$ | Cl | $CONHSO_2CH_3$ | Cl | 166–167 |
| 11 | $CF_3$ | Cl | $CONHSO_2C_4H_9$ | Cl | 122 |
| 12 | $CF_3$ | Cl | $CH_3$<br>$\mid$<br>$-OCHCO_2C_2H_5$ | H | Oil |
| 13 | $CF_3$ | Cl | $-OCH_2CO_2C_2H_5$ | H | Oil |

For convenience the compounds of the invention have been represented above by a single general formula. However the compounds of the invention may be capable of existing in alternative tautomeric forms in whic one or more hydrogen atoms are placed in positions different from those indicated by the formulae of Table I, the chemical bonds of the structural formula being correspondingly rearranged. The structural formulae in this specification are intended to be inclusive of an representative of such alternative tautomeric forms.

Some of the compounds of the invention contain a chiral centre. These may be resolved into optical isomers by conventional methods known in the art. The invention includes the separate optical isomers and their mixtures in all proportions.

Some of the compounds of the invention are acids and form salts with bases. Acidic compounds include those containing a carboxy group and those containing an N-alkanesulphonylcarboxamide group. Both the free acids and their salts may be used as herbicides. Examples of salts include metal salts and salts formed from ammonium and substituted ammonium cations. Among the metal salts are those in which the metal cation is an alkali metal cation for example, sodium, potassium or lithium, or an alkaline earth metal cation, for example calcium or magnesium. The substituted ammonium cations include mono-, di-, tri- and tetra-substituted ammonium cations in which the substituents may be for example an alkyl or alkenyl radical of 1 to 20 carbon atoms optionally containing one or more hydroxy, alkoxy or phenyl substituents.

The compounds of the invention may be prepared in general by reacting a suitably substituted 2- halogenopyridine (II) with an appropriately substituted phenol in presence of a base, as shown in Scheme A.

SCHEME A

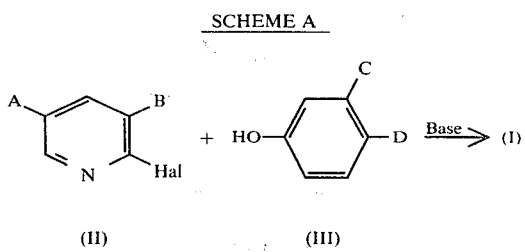

(II)        (III)

Preferably the reaction is carried out in a solvent. The reaction may be accelerated by heating, for example to a temperature in the range from 50° to 150° C., preferably in the range 50° to 100° C. Solvents include for example non-hydroxylic solvents, for example acetone, dimethyl sulphoxide, dimethyl formamide and tetramethylene sulphone. The reaction may be carried out by first forming a metal salt of the phenol in a convenient solvent, for example methanol, removing the methanol, and then adding the non-hydroxylic solvent and the substituted 2-halogenopyridine to the metal salt of the substituted phenol. Suitable metal salts include the sodium and potassium salts.

The halogen substituent in the pyridine (II) may be for example a fluorine, chlorine, bromine or iodine atom, and is preferably fluorine or chlorine. Such 2-halogeno-3,5-A,B-substituted pyridines are known compounds.

In some cases it may be preferred to use Scheme A to prepare a compound in which the substituents C and D are not those which are required to be present in the final product, but which may be converted thereto in a step subsequent to the reaction shown in Scheme A. Thus for example when D is to be a nitro group, the reaction in Scheme A may be carried out using a phenol in which D is hydrogen, and the product from Scheme A may then be nitrated to introduce the required nitro group. Similarly, when C is to be an N-methanesulphonylcarboxamido group, it may be convenient to prepare the compound in which C is a carboxyl group, and then convert this to the N-methanesulphonylcarboxamido group.

The compounds of the invention are useful both as pre- and post-emergence herbicides. Pre-emergence herbicides are usually used to treat the soil in which a crop is to be planted, by application before or during seeding, or after seeding and before the crop emerges. Post-emergence herbicides are applied after the crop plants have emerged from the soil. Compounds of the invention may be used as selective herbicides in a variety of crops, including for example cotton, soya bean, and peas. Compounds of the invention may also be used as total herbicides. The compounds of the invention may be applied by any of the conventional techniques for applying herbicides. When applied as pre-emergence herbicides they may for example be sprayed on the surface of the soil before or during seeding, or after seeding and before emergence of the crop. In some situations for example in pre-emergence application to soya bean crops it may be advantageous to incorporate the compound of the invention into the soil before planting the crop. This may be done by applying the compound to the surface of the soil and then discing or harrowing the soil to mix the compound with the soil. Alternatively use may be made of the applicators which have been developed for placing herbicides in a band beneath the surface of the soil.

In another aspect, therefore, the invention provides a process of killing or severely injuring unwanted plants, which comprises applying to the plants or to the locus thereof, a compound of the formula (I) or a salt thereof as hereinbefore defined.

As will be understood by those skilled in the art, the amount of the compound (I) applied will depend upon a variety of factors, for example the particular compound chosen for use and the identity of the unwanted plants. By way of general guidance, however, an amount of from 0.1 to 5.0 kilograms per hectare is usually suitable, while from 0.25 to 1.0 kilograms per hectare is preferred.

Particular examples of compounds which may be used as selective herbicides in crops of cotton include compounds 3 and 6 of Table I.

A particular example of a compound which may be used as a selective herbicide in crops of soya bean is compound 3 of Table I. Preferably the compound is applied at a rate of 0.1 to 1.5 kilograms per hectare to the area of the soya bean crop. The compound may be applied before or after the emergence of the crop.

The compounds used in the process of the invention are preferably applied in the form of a composition, in which the active ingredient is mixed with a carrier comprising a solid or liquid diluent. In another aspect, therefore, the invention provides a herbicidal composition, comprising as an active ingredient a compound of the formula (I) as hereinbefore defined, in admixture with a solid or liquid diluent. Preferably the composition also comprises a surface-active agent.

The solid compositions of the invention may be for example in the form of dusting powders, or may take the form of granules. Suitable solid diluents include, for example, kaolin, bentonite, kieselguhr, dolomite, calcium carbonate, talc, powdered magnesia, and Fuller's earth. Solid compositions also include soluble powders and granules which may comprise a salt of a compound of the invention in admixture with a water-soluble carrier.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecylbenzenesulphonate, sodium, calcium and ammonium lignosulphonate, butylnaphthalene sulphonate, and a mixture of the sodium salts of diisopropyl- and triisopropylnaphthalenesulphonic acid. Suitable agents of the nonionic type include, for example, the condensation products of ethylene oxide with fatty alcohols such as oleyl alcohol and cetyl alcohol, or with alkyl phenols such as octyl-phenol, nonylphenol, and octylcresol. Other nonionic agents are the partial esters derived from long chain fatty acids and hexitol anhydrides, for example sorbitol monolaurate; the condensation products of the said partial esters with ethylene oxide and the lecithins.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogeneous for a sufficient time to enable them to be applied by conventional spray equipment.

The compositions of the invention may contain, in addition to carriers and surface-active agents, various other constituents to increase their usefulness. They may contain, for example, buffering salts to maintain the pH of the composition within a desired range; antifreeze agents, for example urea or propylene glycol; adjuvants, for example oils and humectants; and sequestrants, for example citric acid and ethylenediaminetetracetic acid, which help to prevent the formation of insoluble precipitates when the compositions are diluted with hard water. Aqueous dispersions may contain anti-settling agents and anti-caking agents. The compositions may in general contain a dye or pigment to impart a characteristic colour. Agents for increasing viscosity may be added to reduce the formation of fine droplets during spraying, and thereby reduce spray drift. Other additives useful for particular purposes will be known to those skilled in the formulation art.

In general concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many uses contain between 0.01% and 10% and preferably between 0.1% and 1% by weight of the active ingredient.

The inventon is illustrated by the following Examples, in which all parts are by weight and all temperatures in degrees Centigrade unless otherwise stated.

EXAMPLE 1

This Example illustrates the preparation of compounds nos 1 and 2 of Table I.

(a) A solution of 3-methoxyphenol (1.24 g) in dry dimethyl sulphoxide (25 ml) was reacted with sodium hydride (0.48 g of 50% dipersion in oil). When reaction was complete, a solution of 2-fluoro-5-trifluoromethylpyridine (1.65 g) in dry dimethyl sulphoxide (15 ml) was added and the mixture heated with stirring to 60°-65° C. for 6 hours. The mixture was cooled, diluted with water and extracted with ether. The ether extract was washed with 2 M sodium hydroxide and then with water, dried and evaporated to give an oil identified as 2-(3-methoxyphenoxy)-5-trifluoromethylpyridine (2.6 g).

(b) The product from (a) (2.5 g) and pyridine hydrochloride (about 10 molar proportions) were fused at 160°-165° for 5¾ hours. The mixture was poured into water, and the mixture acidified and extracted with ether (200 ml). The ether was dried and evaporated to give an oil which partially solidified, and was purified by thin layer chromatography using silica gel as the solid phase (6 plates 20 cm×20 cm with 2 mm layer of silica) and a mixture of chloroform and ethanol (6%) as the eluent.

(c) The 2-(3-hydroxyphenoxy)-5-trifluoromethylpyridine obtained according to (b) above (0.37 g) was heated under reflux with anhydrous potassium carbonate (0.3 g) and ethyl bromopropionate (0.4 g) in methyl ethyl ketone (10 ml) with stirring for 2½ hours. The solution was cooled, filtered, and evaporated to give an oil (0.38 g) identified as compound no 1 by its infra-red spectrum and mass spectrum.

Following the above procedure, but using 2-chloro-5-chlorodifluoromethylpyridine in place of 2-fluoro-5-trifluoromethylpyridine, compound no 2 of Table I was prepared.

EXAMPLE 2

This Example illustrates the preparation of compounds nos 7 and 8 of Table I.

(a) Preparation of compound no. 7 m-Hydroxybenzoic acid (1.32 g) was added with stirring to a solution of potassium hydroxide (1.32 g, 85% pellets) in dry methanol (25 ml) and the mixture stirred for 15 minutes, and evaporated to dryness. The resulting white solid was collected and dry dimethylsulphoxide (15 ml) added. 5-Trifluoromethyl-2,3-dichloropyridine (2.2 g) was then added, followed by anhydrous potassium carbonate (0.5 g). The whole was thoroughly mixed and left overnight, and then for a further 24 hours. The mixture was then poured into cold water (100 ml) and extracted with chloroform. The aqueous layer was acidified with concentrated hydrochloric acid, precipitating a white solid. This was washed with water, and dried to give 2-(3-carboxyphenoxy)-3-chloro-5-trifluoromethylpyridine (2.5 g) with a melting point of 158° C. (compound no. 7).

(b) Preparation of compound no. 8

The product prepared as described in (a) above (3.2 g) was heated under reflux in thionyl chloride (30 ml) for 2 hours, then left overnight at room temperature. The excess of thionyl chloride was removed to give a yellow oil which crystallised on standing. The solid was dissolved in dry pyridine (20 ml) and half of this solution used as below. Methanesulphonamide (0.48 g) was added to the pyridine solution with stirring at room temperature and the whole left to stand at room temperature overnight. The pyridine was then removed under reduced pressure, and the residue dissolved in water and acidified to pH 1. The acid solution was extracted with ethyl acetate. The extract was washed with water, dried and evaporated to give an oil, which was crystallised from a mixture of ethyl acetate and petroleum (b.p. 60°–80°) to yield compound no. 8. (1.35 g) with a melting point of 174° C.

EXAMPLE 3

This Example illustrates the preparation of compound no. 3 of Table I.

(a) Concentrated sulphuric acid (10 ml) and 1,2-dichloroethane (4 ml) were vigorously stirred together at 0° C. for 10 minutes. Compound no. 7 (2.5 g) was added in portions over a period of 10 minutes at 0° C.

Potassium nitrate (0.8 g) was added portionwise over 10 minutes at 0° C. and the resulting mixture stirred at 0° C. for 30 minutes, and then at 10° C. for 10 minutes. The mixture was poured into ice and water and extracted with ethyl acetate. The extract was washed with water, dried and evaporated. The residue was crystallised from a mixture of ethyl acetate and petroleum (b.p. 60°–80°) giving 2-(3-carboxy-4-nitrophenoxy)-3-chloro-5-trifluoromethyl pyridine as a white solid (2.0 g) with m.p. 131° C.

(b) The product from paragraph (a) above (0.9 g) was heated under reflux in thionyl chloride (10 ml) for 2 hours, then left overnight at room temperature. The excess of thionyl chloride was removed under reduced pressure. The remaining oil was dissolved in dry pyridine (5 ml) and methanesulphonamide (0.24 g) was added. The mixture was stirred for 3 hours, and then left overnight. The mixture was kept a further two days at 4° C., and the pyridine then removed under reduced pressure. The residue was mixed with a little toluene and re-evaporated. The yellow oil remaining was dissolved in water, brought to pH 1 with concentrated hydrochloric acid and the mixture extracted with ethyl acetate. The extract was washed with water, dried and evaporated to give an oil. This was purified by thin layer chromatography on silica gel using acetonitrile as solvent. The main band was eluted with ethanol. The eluted product was crystallised from mixture of ether and petroleum (b.p. 40°–60°) at 0° C. to give compound no. 3 (0.25 g), m.p. 175°–176° C.

EXAMPLE 4

This Example illustrates the preparation of compound no. 4 of Table I.

A solution of potassium hydroxide (1.32 g; 85% pellets) in dry methanol (25 ml) was treated at room temperature with metahydroxybenzoic acid (1.38 g) to give a solution. This was stirred for 30 minutes and then coevaporated with added toluene to give a white solid. The solid was dispersed in dry dimethylsulphoxide (10 ml.) Anhydrous potassium carbonate (0.5 g) and 2-chloro-5-trifluoromethylpyridine (1.82 g) were added, and the solution stirred. After 64 hours, water (100 ml) was added. The mixture was extracted with chloroform, filtered and brought to pH 1 with concentrated hydrochloric acid. The solid which precipitated was washed with water and dried to give 2-(3-carboxyphenoxy)-5-trifluoromethylpyridine (2.4 g) (m.p. 146° C.).

This compound was converted into compound no. 4 following the procedure described in Example 3 for compound no. 3.

The remaining compounds in Table I were prepared by the procedures in the foregoing Examples. Thus compound no. 5 was prepared by nitration of 2-(3-carboxyphenoxy)-5-trifluoromethylpyridine following the procedure of Example 3(a) and compound no. 6 was prepared from compound no. 5 following the procedure of Example 3(b).

EXAMPLE 5

This Example illustrates a preparation of compound no. 9 of Table I.

3-Chloro-2-(3-hydroxy-4-nitrophenoxy)-5-trifluoromethylpyridine (0.3 g) and 2-chloro-N-methanesulphonylpropionamide (0.16 g) were heated and stirred under reflux in methyl ethyl ketone with anhydrous potassium carbonate (0.5 g) for 20 hours. The cooled reaction solution was shaken with ethyl acetate and dilute hydrochloric acid. The ethyl acetate layer was washed with water, dried, and evaporated to give a yellow oil. The oil was chromatographed on a silica gel plate (2 mm thick) using ethyl acetate as the solvent. The band at approximately $R_f$ 0.3 was collected. The white solid so obtained was recrystallised from a mixture of ether and hexane to give compound 9 with a melting point of 144°–145° C. The pyridine compound required as starting material was prepared by de-methylation of 3-chloro-2-(3-methoxy-4-nitrophenoxy)-5-trifluoromethylpyridine using pyridine hydrochloride as described in part (b) of Example 1.

EXAMPLE 6

This Example illustrates the herbicidal properties of compound of Table I. The compounds were submitted to herbicide tests as described below.

Each compound was formulated for test by mixing an appropriate amount of it with 5 ml of an emulsion prepared by diluting 160 ml of a solution containing 21.8 grams per liter of Span 80 and 78.2 grams per liter of Tween 20 in methylcyclohexanone to 500 ml with water. Span 80 is a Trade Mark for a surface-active agent comprising sorbitan monolaurate. Tween 20 is a Trade Mark for a surface-active agent comprising a condensate of 20 molar proportions of ethylene oxide with sorbitan monolaurate. The mixture of the compound and the emulsion was then shaken with glass beads and diluted to 40 ml with water. The spray composition so prepared was sprayed on to young pot plants (post-emergence test) of the species named in Table 2 below, at a rate equivalent to 1000 liters per hectare. Damage to plants was assessed 14 days after spraying by comparison with untreated plants, on a scale of 0 to 5 where 0 is 0 to 20% damage and 5 is complete kill. In the table of results, a dash (-) means that no test was made.

A test was also carried out to detect pre-emergence herbicidal activity. Seeds of the test species were placed on the surface of fibre trays of soil and were sprayed with the compositions at the rate of 1000 liters per hectare. The seeds were then covered with further soil. Three weeks after spraying, the seedlings in the sprayed fibre trays were compared with the seedlings in unsprayed control trays, the damage being assessed on the same scale of 0 to 5.

The results of the tests are given in Table II below.

TABLE II

| COMPOUND NO | PRE- OR POST EMERGENCE APPLICATION | RATE OF APPLICATION kg/HA | Sb | Rp | Ct | Sy | Mz | Ww | Rc | Sn | Ip | Am | Pi | Ca | Po | Xs | Ab | Cv | Ot/Av | Dg | Pu | St | Ec | Sh | Ag | Cn |
|---|---|---|---|---|---|---|---|---|---|---|---|---|---|---|---|---|---|---|---|---|---|---|---|---|---|---|
| 1 | Pre | 5 | 3 | 3 | 0 | 0 | 3 | 2 | 5 | — | 0 | 3 | 0 | — | — | 2 | 3 | — | 0 | — | 1 | 4 | 4 | 3 | 4 | 0 |
| 1 | Post | 5 | 2 | 4 | 0 | 0 | 3 | 1 | 2 | 2 | 0 | 4 | 4 | 2 | 5 | 0 | 4 | 3 | 0 | 3 | 0 | 4 | 4 | 4 | 0 | 0 |
| 2 | Pre | 5 | 1 | 2 | 0 | 0 | 0 | 0 | 0 | — | 0 | 2 | 0 | — | — | 2 | 2 | — | 0 | — | 0 | 0 | 2 | 0 | 0 | 0 |
| 2 | Post | 5 | 1 | 3 | 1 | 2 | 2 | 0 | 1 | 3 | 0 | 4 | 3 | 1 | 5 | 0 | 4 | 3 | 0 | 2 | 0 | 4 | 4 | 4 | 2 | 0 |
| 3 | Pre | 1 | 4 | 5 | 1 | 0 | 0 | 3 | 3 | 5 | 0 | 5 | — | 4 | 5 | 2 | 4 | — | 0 | 4 | 0 | 4 | 1 | 4 | 0 | 0 |
| 3 | Post | 3 | 3 | 5 | 2 | 0 | 1 | 3 | 3 | 4 | 5 | 5 | 2 | 3 | 4 | 2 | 4 | 5 | 2 | — | 2 | 5 | 5 | 4 | 3 | 0 |
| 4 | Pre | 5 | 5 | 5 | 0 | 0 | 2 | 4 | 4 | 5 | 3 | 5 | — | 5 | 5 | 5 | 5 | — | 3 | 4 | 0 | 5 | 4 | 5 | 3 | 3 |
| 4 | Post | 5 | 5 | 5 | 2 | 4 | 4 | 4 | 3 | 5 | 5 | 5 | 4 | 3 | 5 | 4 | 5 | 5 | 3 | — | 2 | 5 | 5 | 4 | 4 | 2 |
| 5 | Pre | 5 | 2 | 4 | 0 | 0 | 1 | 0 | 1 | 4 | 3 | 4 | 3 | 3 | 4 | 0 | 3 | 4 | 0 | — | 2 | 4 | 4 | 4 | 2 | 0 |
| 5 | Post | 5 | 4 | 2 | 0 | 0 | 0 | 3 | 2 | 2 | 5 | 3 | — | 2 | 5 | 1 | 1 | — | 2 | 4 | 0 | 4 | 3 | 4 | 3 | 2 |
| 6 | Pre | 5 | 4 | 4 | 0 | 0 | 1 | 3 | 1 | 4 | 4 | 5 | 4 | 4 | 5 | 1 | 4 | 4 | 2 | — | 0 | 5 | 5 | 4 | 2 | 2 |
| 6 | Post | 5 | 4 | 4 | 0 | 1 | 3 | 1 | 2 | 4 | 0 | 5 | — | 3 | 5 | 0 | 0 | — | 1 | 4 | 1 | 3 | 1 | 2 | 2 | 1 |
| 7 | Pre | 5 | 3 | 4 | 1 | 0 | 3 | 3 | 0 | 5 | 4 | 5 | 1 | 4 | 3 | 1 | 4 | 4 | 1 | — | 1 | 4 | 2 | 2 | 0 | 0 |
| 7 | Post | 5 | 0 | 2 | 0 | 1 | 1 | 0 | 0 | 0 | 0 | 4 | — | 3 | 2 | 0 | 3 | — | 0 | 2 | 0 | 4 | 0 | 0 | 0 | 2 |
| 8 | Pre | 5 | 0 | 2 | 0 | 2 | 1 | 0 | 0 | 0 | 0 | 5 | 1 | 0 | 2 | 0 | 2 | 2 | 0 | — | 1 | 4 | 4 | 1 | 0 | 0 |
| 8 | Post | 5 | 1 | 1 | 0 | 4 | 2 | 1 | 0 | 5 | 0 | 4 | — | 4 | 5 | 0 | 4 | — | 0 | 4 | 0 | 4 | 0 | 4 | 0 | 0 |
| 9 | Pre | 0.01 | 3 | 5 | 2 | 4 | 2 | 1 | 1 | 4 | 5 | 5 | 4 | 4 | 5 | 4 | 5 | 5 | 0 | — | 4 | 5 | 5 | 4 | 3 | 0 |
| 9 | Post | 0.01 | 0 | 0 | 0 | 0 | 0 | 0 | 0 | 1 | 0 | 0 | — | 0 | — | — | 0 | — | 0 | 0 | — | 0 | 0 | 0 | 0 | — |
| 9 | Pre | 0.20 | 4 | 4 | 0 | 2 | 0 | 0 | 1 | 5 | 2 | 4 | — | 4 | — | — | 4 | 3 | 0 | 4 | 1 | 4 | 0 | 3 | 1 | — |

TABLE II-continued

| COMPOUND NO | PRE - OR POST EMERGENCE APPLICATION | RATE OF APPLICATION kg/HA | TEST PLANTS | | | | | | | | | | | | | | | | | | | |
|---|---|---|---|---|---|---|---|---|---|---|---|---|---|---|---|---|---|---|---|---|---|---|
| | | | Sb | Rp | Ct | Sy | Mz | Ww | Rc | Sn | Ip | Am | Pi | Ca | Po | Xs | Ab | Cv | Ot/Av | Dg | Pu | St | Ec | Sh | Ag | Cn |
| | Post | | 4 | 5 | 3 | 4 | 3 | 4 | 1 | 5 | 5 | 5 | — | — | — | 5 | 5 | — | 3 | 3 | — | 5 | 5 | 5 | 2 | — |

(The results for Compound 9 are from assessment at 13 days)
Names of test plants in Table II
Sb Sugar beet
Rp Rape
Ct Cotton
Sy Soya bean
Mz Maize
Ww Winter wheat
Rc Rice
Sn *Senecio vulgaris*
Ip *Ipomoea purpurea*
Am *Amaranthus retroflexus*
Pi *Polygonum aviculare*
Ca *Chenopodium album*
Po *Portulaca oleracea*
Xs *Xanthium spinosum*
Ab *Abutilon theophrastii*
Cv *Convolvulus arvensis*
Ot/Av Oats (cultivated in pre-emergence test and *Avena fatua* (wild oats) in post-emergence test).
Dg *Digitaria sanguinalis*
Pu *Poa annua*
St *Setaria viridis*
Ec *Echinochloa crus-galli*
Sh *Sorghum halepense*
Ag *Agropyron repens*
Cn *Cyperus rotundus*

We claim:

1. A phenoxypyridine of the formula (I):

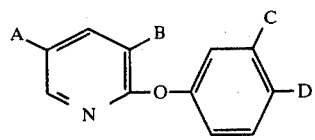

wherein each of A and B is a hydrogen atom, a fluorine, chlorine, bromine or iodine atom, or a difluoromethyl, chlorodifluoromethyl or trifluoromethyl group, provided that at least one of A and B is a halomethyl group; C is an $-OR^1$ group wherein $R^1$ is an alkyl group of 1 to 12 carbon atoms substituted by a $-COZ$ group wherein Z is a group $-NR^4R^5$ wherein $R^4$ is hydrogen, $C_1-C_{12}$ alkyl, or $C_3-C_{12}$ alkenyl, and $R^5$ is alkanesulphonyl of 1 to 6 carbon atoms; and D is nitro or cyano, or a herbicidally acceptable salt thereof.

2. A compound as claimed in claim 1 wherein A is a trifluoromethyl group, B is hydrogen or chlorine, and C is an

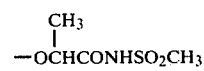

group.

3. A compound as claimed in claim 1 wherein D is nitro.

4. N-methanesulphonyl 2[2-nitro-5-(3-chloro-5-trifluoromethylpyridyl-2-oxy)phenoxy]propionamide.

5. A herbicidal-composition comprising as an active ingredient a herbicidally effective amount of a compound as claimed in claim 1, in admixture with a carrier comprising a solid or liquid diluent.

6. A process of killing or severely damaging unwanted plants, which comprises applying to the plants, or to the locus thereof, a herbicidally effective amount of a compound of the formula (I) of claim 1 or a herbicidally effective amount of a salt thereof as defined in claim 1.

* * * * *